United States Patent [19]
Girvin et al.

[11] Patent Number: 6,061,132
[45] Date of Patent: May 9, 2000

[54] DUAL DETECTOR ARRAY WITH NOISE CANCELLATION FOR A PARTICLE SIZE DETECTION DEVICE

[75] Inventors: Kenneth L. Girvin, Grants Pass; Richard K. DeFreez, Azalea, both of Oreg.

[73] Assignee: Pacific Scientific Instruments Company, Grants Pass, Oreg.

[21] Appl. No.: 09/119,379

[22] Filed: Jul. 20, 1998

[51] Int. Cl.[7] .................................................. G01N 15/14
[52] U.S. Cl. .......................... 356/336; 356/343; 356/339; 250/574
[58] Field of Search .................... 356/335–343; 250/574, 575, 208.2

[56] References Cited

U.S. PATENT DOCUMENTS

| | | | |
|---|---|---|---|
| 4,746,215 | 5/1988 | Gross | 356/339 |
| 4,798,465 | 1/1989 | Knollenberg | 356/336 |
| 4,893,928 | 1/1990 | Knollenberg | 356/336 |
| 4,984,889 | 1/1991 | Sommer | 356/336 |
| 5,011,286 | 4/1991 | Petralli | 356/343 |
| 5,084,629 | 1/1992 | Petralli | 250/573 |
| 5,282,151 | 1/1994 | Knollenberg | 356/336 |
| 5,642,193 | 6/1997 | Girvin et al. | 356/339 |
| 5,805,281 | 9/1998 | Knowlton et al. | 356/343 |
| B1 4,798,465 | 9/1991 | Knollenberg | 356/336 |

*Primary Examiner*—Hoa Q. Pham
*Attorney, Agent, or Firm*—Stoel Rives LLP

[57] ABSTRACT

In a particle detector, a stream carrying particles to be measured is passed through a laser beam. A pair of optical collection systems are arranged perpendicular to the laser beam, opposing each other. The optical collection system reflects light signals indicative of particles sensed in the sensing region to a pair of detector arrays. Each detector array has a plurality of detectors to detect the particle signals, as well as other noise. One detector from each array monitors the same sensing region. The signals from the detectors are processed through a noise cancellation circuit. The noise cancellation circuit first amplifies each detector signal through a photo-amp. Then, the signals of the detectors in one detector array are paired up with corresponding signals of detectors, spaced at least two detectors away, in the other detector array. The paired-up signals pass through differential amplifiers, which essentially cancel the light fluctuation noise. The remaining particle signals are further processed through an A/D converter to a user interface. The dual detector array is able to achieve a better than 0.10 micron sensitivity at a particle flow of 1.0 cubic foot per minute.

12 Claims, 2 Drawing Sheets

DUAL DETECTOR ARRAY WITH NOISE CANCELLATION FOR A PARTICLE SIZE DETECTION DEVICE

FIELD OF THE INVENTION

This invention relates to particle detection, and, more particularly to particle detection using a dual detector array.

BACKGROUND OF THE INVENTION

Systems for measuring sizes of particles by detecting scattered light from the particles as they pass through a beam of light are known in the prior art. Among the constant challenges are attempting to improve the resolution of the particle signals that are detected and reducing the amount of the background noise that is generated. The background that is generated can include several types of noise including molecular noise, shot noise, light fluctuation noise, photo-amp noise and turbulence noise. The type of noise that most influences the effectiveness of particle sensors is light fluctuation noise, especially in high power intracavity laser sensors. Fluctuations in the laser beam travel at the speed of light, and compared to the speed of the photo-amp, it is effectively fluctuating at the same time all along the beam. Air molecules in the view volume scatter the light fluctuation noise. It is desirable to eliminate this type of noise from particle sensing devices.

Advances in the development of optical particle sensors are continuously being sought after to increase the sensitivity of particle sensors especially at higher flow rates. It is desirable to achieve a higher flow rate without increasing the velocity of the sample stream. The methods described in U.S. Pat. Nos. 5,011,286 and 5,084,629 to Petralli, splits the flow into separate ports to reduce the velocity and background light level per detector. High particle velocity on the detector has two adverse effects, it creates flow turbulence (when the Reynolds number exceeds 2000) and it reduces the output signal because of photo-amp frequency response limitations. One way to maintain low velocity would be to use a larger nozzle to cover a large view volume in the sensor, such as the type described in U.S. Pat. No. 4,746,215 to Gross. However, for example, if the flow rate of a 0.1 cfm sensor was increased to 1.0 cfm, then the view volume and detector would need to be ten times larger. Because of the increased collection of background light noise and photo detector noise, the resulting larger detector would have a signal including ten times as much noise. A practical method to detect the larger view volume light scatter is to use arrays of small detectors. To reduce background light noise even further requires noise cancellation. Thus, the method of signal processing and noise cancellation is crucial to the performance of a sensor.

Various prior art approaches utilize detector arrays to increase the ratio of scattered light from a particle to the background Rayleigh light. These methods reduce background noise by using smaller detectors; therefore, less background is sensed per detector. The higher the ratio of particle scattered light to the background scattered light, the better signal-to-noise ratio. U.S. Pat. Nos. 4,798,465 and 4,893,928 to Knollenberg disclose a detection device to determine particle size from particle effected light scattering in a sensing region illuminated by a laser beam and receiving the particles in a medium, such as air. A linear array of detectors is positioned so that each detector monitors a different portion of the sensing region and provides an electrical output signal that indicates that a particle presence was sensed in the portion that was monitored. The output signals from the detectors are parallel processed and are combined at noise cancellation units with the output signals from other detectors monitoring non-adjacent portions of the sensing region.

In U.S. Pat. No. 4,984,889, Sommer discloses a system to measure particle size using coincidence detection. Light scattered in two different directions from a laser beam by particles are detected by photo-detectors and a coincidence circuit detects simultaneous pulses generated by both photodetectors to discriminate against noise and to disable the integration function in baseline control circuits for preamplifiers amplifying the output signals from the photodetectors.

Other array patents require the particle image to be fixed in space, which is done by having the particle travel towards the collection system. Other prior art methods are not cost effective. None of the prior art methods take all of the necessary steps to significantly reduce most of the light fluctuation noise while detecting the majority of the view volume.

SUMMARY OF THE INVENTION

The present invention improves upon the prior art by allowing for greater coverage of the sensing region for particle detection and by enhancing the signal-to-noise ratio of the output signals detected by the particle detection system. It is the object of this invention to increase sensitivity of the sensor and significantly reduce detected laser noise. It is a further object to produce a cost-effective sensor that achieves better than 0.10 micron sensitivity at a flow rate of 1.0 cubic foot per minute.

In a particle detection system, a stream carrying particles to be measured is passed through a light source, such as a laser beam. Two separate arrays of detectors are arranged to monitor the same view volume. In many of the prior art systems, a single array detection system that includes noise cancellation is used. The disadvantage of this type of system is that a certain number of detectors are assigned to the function of noise detection, so they are lost as signal detectors. For example, if a system is used in which every other detector is used for noise cancellation, then half of the array is not detecting particles, rendering the sensor half blind to particles passing through the view volume. Additionally, this could lead to erroneous results. If particle signals were somehow recoverable from the noise cancellation detectors, and if two simultaneous particles pass through the two detectors that are being subtracted, then the resulting output would be in error because the two signals would be subtracted and counted as one smaller particle or would be cancelled. In the present invention, since there are two separate detector arrays, if a detector in one detection array is detecting noise at a particular time, the corresponding detector in the other detection array is still available to detect a particle signal occurring at the same time.

The present invention also includes a circuit for noise cancellation. The signal of each detector in the one detector array is paired up with the signal of an adjacent detector in the other detector array. The pair of signals are then input to a differential amplifier in order to cancel the noise. The signal remaining is primarily the signal indicative of sensed light generated by particles within the sensing region.

Additionally, another benefit of this invention is to achieve better signal resolution. One of the methods to measure resolution that is widely used for characterizing particle counter performance, is defined in the Japanese Industrial Standard (JIS) number, JIS B9921-1989. The standard explains a method to measure the resolution at the sensitivity limit through the use of a multi-channel analyzer (MCA). The MCA measures and displays the number of signal counts per channel versus signal amplitude. The number of counts of the particle signal is required to be more than twice the number of counts with the lowest counts between the signal and the noise. The particle signals from single sized poly-styrene-latex (PSL) spheres are theoretically supposed to have the same amplitude. But in practice, the signals from the spheres usually do not have the same amplitude due to a variety of reasons, such as light fluctuations, particle size tolerance and flow variations in the view volume. Typically, most of the spread in "peak-to-peak" amplitude, of single sized particle signals near the sensitivity limit, is caused by the amplitude of "peak-to-peak" noise. Smaller detectors and noise cancellation help to reduce the "peak-to-peak" noise, and thereby reduce the amplitude spread and improve the resolution of the signal. The present invention reduces the noise and provides better signal resolution to assist in meeting the JIS specifications for particle counter performance noted above.

BEST MODE FOR CARRYING OUT THE INVENTION

The signal collection system and array placement are known in the prior art (U.S. Pat. No. 4,984,889 to Sommer which is assigned to the same assignee as the present invention). Since the inventive aspect of this invention is in the signal processing methods, other similar sensor collection systems may be used so long as they include the essential features noted herein.

Figure 1:
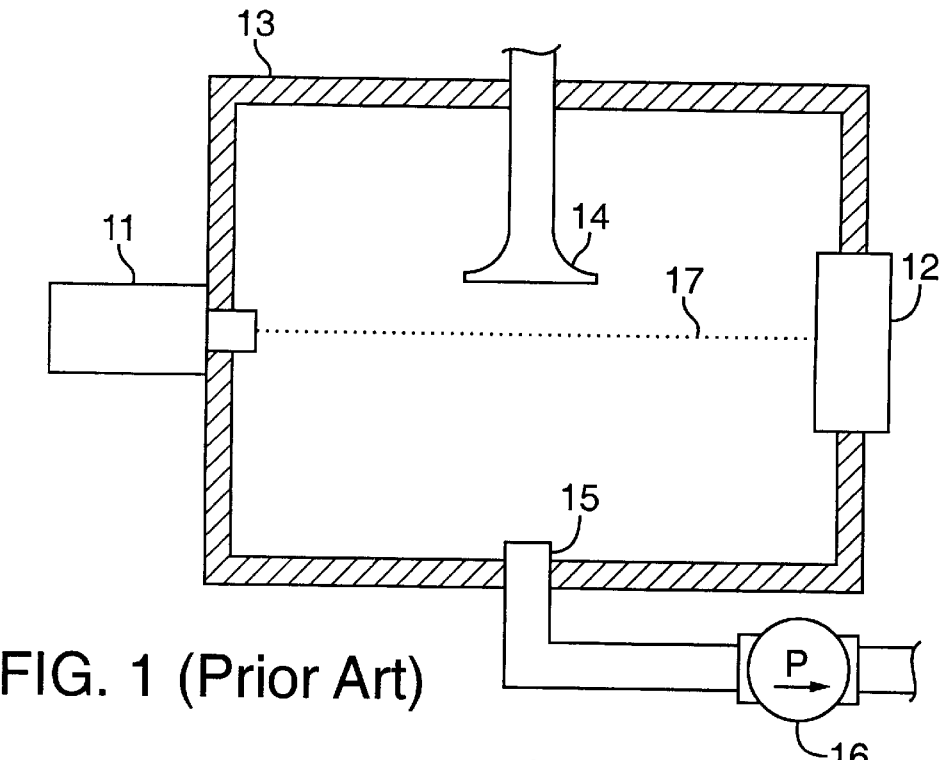
FIG. 1 is a plan view showing a measuring cell as known in the prior art.

In the preferred method of establishing a view volume for signal collection, shown in FIG. 1, a laser beam 17 is generated in an internal cavity of a laser 11, between an end mirror 12 and the laser 11. The laser 11 would be used to illuminate the view volume. The type of laser used could include intra-cavity, external cavity, passive output or another type of laser. In the preferred embodiment, an intracavity laser is used. This type of laser is described in U.S. Pat. No. 5,642,193 to Girvin et al., which is assigned to the same assignee as the present invention. The internal cavity of the laser extends across a particle detecting cell 13 and receives a particle-carrying gas stream that is provided by a nozzle 14, collected by an exit port 15, and pumped from the exit port 15 by a pump 16, which controls the rate of air flow through the laser beam 17. The laser beam 17 is arranged relative to the gas stream in the particle detecting cell 13 so that laser beam 17 passes through the stream parallel to the long dimension of the cross section of the stream. The nozzle 14 shapes the fluid flow through the view volume and is used as described in U.S. Pat. No. 4,746,215 to Gross, which is assigned to the same assignee as the present invention. The nozzle 14 has a width that is approximately matched to that of the beam, and the fluid flow in the view volume can be laminar or turbulent. Sensors with flow rates of 1 cfm, 2 cfm, or other flow rates, could be designed.

In a typical arrangement, the nozzle exit size will be about 1 mm wide by 20 mm long. The laser beam 17 will be about 1 mm in diameter. The nozzle 14 would be positioned such that the length is aligned parallel to the beam 17 and is positioned about 4 mm above the beam 17. This makes the view volume about 1 mm by 1 mm by 20 mm.

Figure 2:
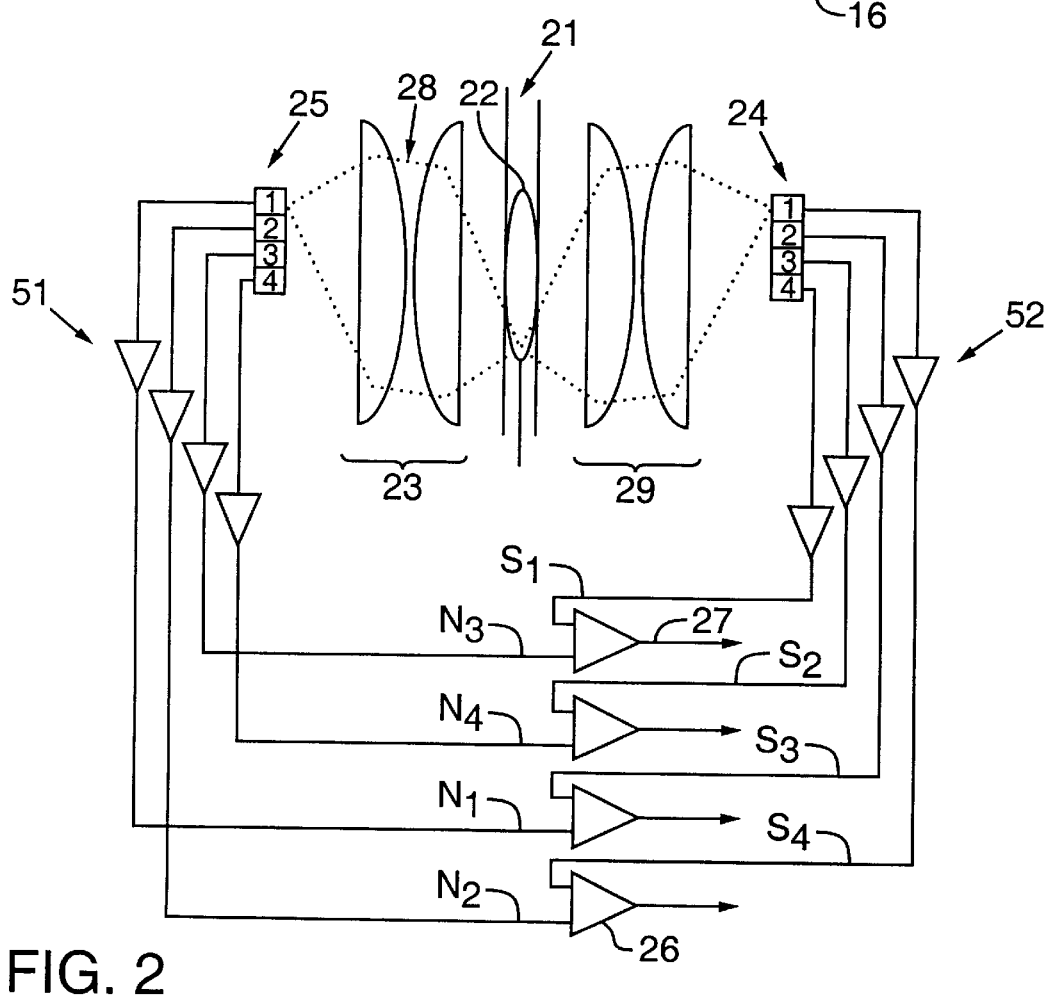
FIG. 2 is a schematic diagram illustrating the collection means, detector arrays and noise cancellation circuit of the present invention.

FIG. 2 shows a schematic diagram of the collection means, detector arrays and signal processing circuits of the present invention. The sample exhaust stream from the nozzle 22 is passed through the view volume, and any particle in the sample stream will pass through the laser beam 21. Two identical collection systems 23 and 29, made up of lenses, are arranged orthogonal to the laser beam 21, opposing each other. Two detector arrays 24 and 25, made up of a plurality of photodetectors (such as photodiodes, CCD elements or photomultipliers), are arranged to receive the collected light from the same area in the view volume. The collection systems 23 and 29 are designed to re-image the scattered light 28 in the view volume onto the arrays 24 and 25 with very high numerical aperture. Each array 24 and 25 collects a similar type and amount of light from the view volume, so that the light amplitude, collection angle and polarities are very similar. Each detector array 24 and 25 contains a similar size and number of photodetectors placed in a row with minimal spacing. Typically, this is carried out on a single silicon chip with detector spacing on the order of microns apart. The size of the detector is determined by the ratio of particle scattered light to the background light. The number of detectors is then determined by the number of detectors required to cover the view volume. Typically, from 20 to 100 silicon photodiodes are used for detectors in an array. (In FIG. 2, only four detectors per array are shown.)

The main improvement over the prior art in this invention is in the cancellation of the light fluctuation noise within the view volume. As shown in FIG. 2, the two arrays 24 and 25 have outputs that are arranged to cancel the light fluctuation noise. One detector array 24 is used to detect signals from particles, and the other detector array 25 is used to detect noise. Using a separate array for noise detection allows full viewing of the sample stream by the signal detector array and allows noise sensing in close proximity. The collected light on each array includes the light fluctuation noise. In high-power intra-cavity laser sensors, the light fluctuation noise can be orders of magnitude greater than that of all of the other noise signals combined.

The signal processing from the detector arrays is arranged such that light fluctuation noise is cancelled from the particle signal in the following manner. The output signals of the photodetectors in the detector arrays 24 and 25 are first amplified by photoamplifiers 51 and 52, which creates a photo-amp combination. A photo-amp from the signal array 24 is paired up with a photo-amp from the noise cancellation array 25 and the photo-amps are connected to difference amplifiers 26. In each difference amplifier 26, the light fluctuation noise signals are subtracted, leaving any uncorrelated signals, such as particle signals as the signal output 27. The paired up photoamplifiers do not view the same portion of the view volume, because this would cause the particle signal to also be cancelled. Instead an adjacent photo-amp, at least two segments away, is used to help prevent subtraction errors. If the collection system cannot image all the particle scattered light on one detector, a small amount may spill over on the next adjacent detector. If that detector were used for noise cancellation, then it could cause an error in the difference amp result. It also relaxes the alignment needs and allows for mechanical tolerance in the assembly. If the image system is good enough to image all of the light onto one detector, then the next adjacent detector can be used to subtract the noise. For example, in FIG. 2, the signal S1 from the photo-amp of detector 1 of the signal array 24 is paired up with the signal N3 from the photo-amp of detector 3 of the noise cancellation array 25. This pattern of pairing up photo-amps and passing the signals through difference amplifiers to cancel noise is repeated down through the entire detector array.

The advantage of using a cancellation photo-amp in close proximity to a signal photo-amp is important when a diverging beam is used in this system. If there is a large separation between the paired photo-amps on a diverging beam, then the photo-amps see different light intensities, which can affect the response of the photo-amps and lead to poor noise cancellation. Close spacing of the paired photo-amps also help when there is turbulent flow. Turbulence can have boundary layers which form cells greater than the size of the detector. These boundary layers can scatter light. The closer that the pair of photo-amps are in relation to each other in the view volume, without being immediately adjacent, the better the cancellation of turbulence light scatter noise. The common part of the signal within the bandwidth of the photo-amp, such as laser light fluctuation noise, is subtracted and for the most part eliminated in real time. The remaining photo-amp output consists of particle signals and other types of noise (such as molecular scatter noise, shot noise and photo-amp noise), which can be orders of magnitude less than the laser light fluctuation noise. The amplitude of an output signal directly proportional to the sixth power of the particle size (below the wavelength of the illumination light).

Figure 3:
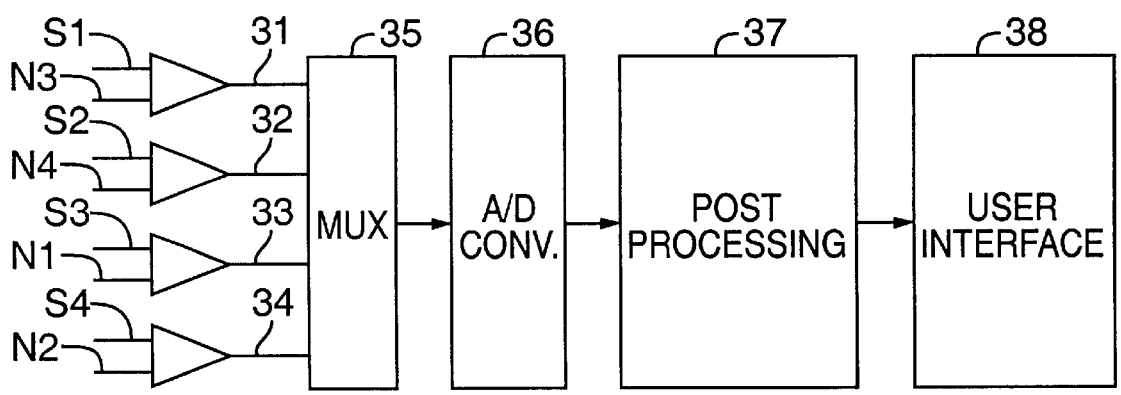
FIG. 3 is a block diagram showing the remainder of the signal processing means following the noise cancellation circuit of the present invention.

Referring to FIG. 3, the outputs of the differential amplifiers 31 through 34 could be multiplexed 35 and then connected to an analog-to-digital converter ADC 36. The ADC 36 would use thresholds to determine if the particle signal amplitude meets a predetermined particle size criterion. If the signal amplitude meets this criterion, the signal is counted as a particle with a size that corresponds to the signal size. The ADC 36 will not detect particles that are seen by the noise photo-amps. The output of the ADC is post-processed 37 and is sent to the user interface 38, as is typically done with portable particle counters. Calibration of the sensors would be carried out in the same way as in a normal particle counter. A range of known, sized particles is sampled, and the resulting output amplitudes are measured (for each size). A multi-channel analyzer can be used to measure the output amplitudes. This is typically done over the dynamic range of sensitivity. Thresholds, of the counter electronics that the sensor is sold with, are set to correspond to increments of the size such 0.08, 0.10, 0.20, 0.30, 0.50 and 1.0 microns. A final check or count comparison against a known good "standard" counter of either the same type or a condensation nucleus counter (CNC) is typically done by introducing the same concentration of particles from a single source to each counter.

What is claimed is:

1. A dual detector array with noise cancellation for a particle counter, comprising:
    a view volume having a fluid flowing therethrough, the fluid carrying particles, with a light source having a beam directed through the view volume;
    a pair of optical collection systems arranged transversely to the beam to collect light scattered by particles carried by the fluid flowing through the view volume, the optical collection systems opposing each other;
    first and second detector arrays, each array receiving light propagating from a different one of the optical collection systems and including a plurality of detectors, each detector providing an electrical output that can include both light fluctuating noise and particle signals indicative of sensed light scattered by particles within a predetermined sensing region, different sets of corresponding detectors in the first detector array and the second detector array sensing different common areas of the sensing region; and
    an output circuit receiving and processing preassigned groups of electrical outputs of the first and second detector arrays, the preassigned groups of outputs of the circuit being established to substantially reduce the likelihood that the processing of the outputs representing corresponding sets of detectors sensing the common areas of the sensing region cancels concurrent particle signals indicative of sensed light scattered by particles within the common areas of the sensing region so that the processing removes most of the light fluctuating noise from the particle signals to increase their signal-to-noise ratios.

2. A dual detector array with noise cancellation for a particle counter, as in claim 1, wherein the output circuit comprises:
    a plurality of photoamplifiers, each photoamplifier having an input receiving one of the electrical outputs of detectors in the first or second detector array and providing a photoamplifier signal output; and
    a plurality of differential amplifiers, each differential amplifier having differential amplifier inputs and producing an output; the differential amplifier inputs of each differential amplifier receiving a photo-amp output signal of a detector in the first detector array and a photo-amp output signal of a detector in the second detector array, the detector in the first detector array and the detector in the second array being not directly spatially opposing.

3. A dual detector array with noise cancellation for a particle counter, as in claim 2, wherein the detectors in the first and the second detector arrays that are not directly spatially opposing are spaced at least two detector positions away from each other.

4. A dual detector array with noise cancellation for a particle counter, as in claim 1, wherein the detectors are charge-coupled devices, photomultipliers, or photodiodes.

5. A dual detector array with noise cancellation for a particle counter, as in claim 1, further comprising particle determining circuitry for determining the existence of a particle in the view volume.

6. A dual detector array with noise cancellation for a particle counter, as in claim 5, wherein the particle determining circuitry includes a multiplexer and an analog-to-digital converter.

7. A dual detector array with noise cancellation for a particle counter, as in claim 1, wherein the detectors are capable of sensing particles having a diameter of about 0.1 micron.

8. A dual detector array with noise cancellation for a particle counter, as in claim 1, wherein the output circuit receiving the electrical outputs of the first and second detector arrays subtractively processes the preassigned groups of outputs from the arrays so that the particle signals are indicative of sensed light generated by particles within the sensing region.

9. A dual detector array with noise cancellation for a particle counter, comprising:
    a view volume having a fluid flowing therethrough, the fluid carrying particles, with a light source having a beam directed through the view volume;

a pair of optical collection systems arranged orthogonally to the beam to collect light scattered by particles carried by fluid flowing through the view volume, the optical collection systems arranged to oppose each other;

first and second detector arrays, each array receiving light propagating from a different one of the optical collection systems and including a plurality of detectors, each detector providing an electrical output that can include both light fluctuating noise and particle signals indicative of sensed light scattered by particles within a predetermined sensing region, each detector from the first detector array sensing a same predetermined sensing region as a detector from the second detector array;

a noise cancellation circuit including a plurality of photoamplifiers to amplify the outputs of detectors in the first and second detector arrays, a plurality of differential amplifiers to subtractively process the electrical outputs of the first and second detector arrays, each differential amplifier having an output and having inputs that include a photoamplifier output signal of a detector in the first detector array and a photoamplifier output signal of a detector in the second detector array, the detector in the first detector array and the detector in the second detector array being not directly spatially opposed, and the differential amplifier outputs providing signals indicative of sensed light scattered by particles within the predetermined sensing region.

10. A dual detector array, as in claim 9, wherein the detector in the first and the second detector arrays are spaced at least two detector positions away from each other.

11. A dual detector array, as in claim 9, wherein the detectors are capable of sensing particles having a diameter of about 0.1 micron.

12. A dual detector array, as in claim 9, wherein the detectors are charge-coupled devices, photomultipliers, or photodiodes.

* * * * *